US008795987B2

(12) United States Patent (10) Patent No.: US 8,795,987 B2
Huynh et al. (45) Date of Patent: Aug. 5, 2014

(54) RIBONUCLEIC ACID INTERFERENCE MOLECULES OF ORYZA SATIVA

(75) Inventors: Tien Huynh, Yorktown Heights, NY (US); Isidore Rigoutsos, Astoria, NY (US)

(73) Assignee: International Business Machines Corporation, Armonk, NY (US)

( * ) Notice: Subject to any disclaimer, the term of this patent is extended or adjusted under 35 U.S.C. 154(b) by 1120 days.

(21) Appl. No.: 12/183,204

(22) Filed: Jul. 31, 2008

(65) Prior Publication Data

US 2008/0311659 A1 Dec. 18, 2008

Related U.S. Application Data

(63) Continuation-in-part of application No. 11/351,951, filed on Feb. 10, 2006.

(60) Provisional application No. 60/652,499, filed on Feb. 11, 2005.

(51) Int. Cl.
 *C12P 19/34* (2006.01)
 *C07H 21/04* (2006.01)
 *C07H 21/02* (2006.01)

(52) U.S. Cl.
 USPC .................. 435/91.1; 536/23.1; 536/24.5

(58) Field of Classification Search
 CPC .................. C12Q 2525/207; C12Q 2525/101; C12Q 1/6827
 See application file for complete search history.

(56) References Cited

U.S. PATENT DOCUMENTS

| | | | |
|---|---|---|---|
| 6,108,666 A | 8/2000 | Floratos et al. | |
| 2008/0113342 A1 | 5/2008 | Cao et al. | |

OTHER PUBLICATIONS

Altschul et al., Basic Local Alignment Search Tool, J Mol Biol., vol. 215, pp. 403-410, 1990.
Chenna et al., Multiple Sequence Alignment with the Clustal Series of Programs, Necleic Acids Research, vol. 31, No. 13, pp. 3497-3500, 2003.
Jiang et al., Pack-Mule Transposable Elements Mediate Gene Evolution in Plants, Nature Publishing Group, vol. 431, 569-573, Sep. 2004.
Lim et al., Vertebrate MicroRNA Genes, Science Magazine, vol. 299, p. 1540, Mar. 2003.
Wooton et al., Statistics of Local Complexity in Amino Acid Sequences and Sequence Databases, Computer and Chemistry, vol. 17, No. 2, pp. 149-163, 1993.
Matthews et al., Expanded Sequence Dependence of Thermodynamic Parameters Improves Prediction of RNA Secondary Structure, J. Mol. Biol., vol. 288, pp. 911-940, 1999.
Ashburner et al., Gene Ontology: Tool for the Unification of Biology, The Gene Ontology Consortium, Nature Genetics, vol. 25, pp. 25-29, May 2000.
Griffiths-Jones et al., Rfam: An RNA Family Database, Nucleic Acids Research, vol. 31, No. 1, pp. 439-441, 2003.
Jorgensen, Restructuring the Genome in Response to Adaptive Challenge: McClintock's Bold Conjecture Revisited, Cold Spring harbor Symposia on Quantitative Biology, vol. LXIX, pp. 349-354, 2004.
Lim et al., The MicroRNAs of *Caenorhabditis elegans*, Genes and Development, vol. 17, pp. 991-1008, 2003.
Xie et al., Systematic Discovery of Regulatory Motifs in Human Promotes and 3' UTRs by Comparison of Several Mammals, Nature Publishing Group, vol. 434, pp. 338-345, Mar. 2005.
Rehmsmeier et al., Fast and Effective Prediction of MicroRNA/Target Duplexes, RNA, vol. 10, pp. 1507-1517, 2004.
Bejerano et al., Ultraconserved Elements in the Human Genome, Science Magazine, vol. 304, pp. 1321-1325, May 2004.
Hofacker et al., Fast Folding and Comparison of RNA Secondary Structures, Monatshefte fur Chemie (Chemical Monthly), vol. 125, pp. 167-188, 1994.
Lai et al., Computational Identification of *Drosophila* MicroRNA Genes, Genome Biology, vol. 4, Issue 7, Article R42, pp. 1-20, 2003.
Rigoutsos et al., Combinatorial Pattern Discovery in Biological Sequences: The Teiresias Algorithm, Bioinformatics, vol. 14, No. 1, pp. 55-67, 1998.
Berezikov et al., Phylogenetic Shadowing and Computational Identification of Human MicroRNA Genes, Cell, vol. 120, pp. 21-24, 2005.
Stark et al., Identification of *Drosophila* MicroRNA Targets, PLoS Biology, vol. 1, Issue 3, pp. 397-409, 2003.
Bentwich et al., Identification of Hundreds of Conserved and Nonconserved Human microRNAs, Nature Genetics, vol. 37, No. 7, pp. 766-770, Jul. 2005.
Iwashita et al., A Transposable Element-Mediated Gene Divergence that Directly Produced a Novel Type Bovine Bent Protein Including the Endonuclease Domain of RTE-1, Mol Biol Evol. vol. 20, No. 9, pp. 1556-1563, 2003.
Lev-Maor et al., The Birth of an Alternatively Spliced Exon: 3' Splice-Site Selection in Alu Exons, Science Magazine, vol. 300, pp. 1288-1291, May 2003.
Stabenau et al., The Ensemble Core Software Libraries, Genome Research, vol. 14, pp. 929-933, 2004.
Enright et al., MicroRNA Targets in *Drosophila*, Genome Biology, vol. 5, Issue 1, Article R1, pp. 1-14, 2003.
U.S. Appl. No. 11/352,152, filed Feb. 10, 2006 titled Ribonucleic Acid Interference Molecules.
U.S. Appl. No. 11/351,821, filed Feb. 10, 2006 titled System and Method for Identification of MicroRNA Target Sites and Corresponding Targeting MicroRNA Sequences.

(Continued)

*Primary Examiner* — Amy Bowman
(74) *Attorney, Agent, or Firm* — Ryan, Mason & Lewis, LLP

(57) ABSTRACT

Sequences of ribonucleic acid interference molecules are provided. For example, in one aspect, at least one nucleic acid molecule comprising at least one of one or more precursor sequences having SEQ_ID NO: 1 through SEQ_ID NO: 11,928 and one or more corresponding mature sequences having SEQ_ID NO: 11,929 through SEQ_ID NO: 24,555 is provided. Techniques are also provided for regulating gene expression.

7 Claims, No Drawings

(56) References Cited

OTHER PUBLICATIONS

U.S. Appl. No. 11/351,951, filed Feb. 10, 2006 titled System and Method for Identification of MicroRNA Precursor Sequences and Corresponding Mature MicroRNA Sequences from Genomic Sequences.

U.S. Appl. No. 11/367,512, filed Feb. 10, 2006 titled Techniques for Linking Non-Coding and Gene-Coding Deoxyribonucleic Acid Sequences and Applications Thereof.

U.S. Appl. No. 11/217,784, filed Aug. 31, 2005 titled Methods and Apparatus for Incremental Approximate Nearest Neighbor Searching.

U.S. Appl. No. 12/183,166, filed Jul. 31, 2008 titled Ribonucleic Acid Interference Molecules of *Arabidopsis Thaliana*.

RIBONUCLEIC ACID INTERFERENCE MOLECULES OF ORYZA SATIVA

CROSS-REFERENCE TO RELATED APPLICATIONS

The present application is a continuation-in-part of, and claims priority to, U.S. patent application entitled "System and Method for Identification of MicroRNA Precursor Sequences and Corresponding Mature MicroRNA Sequences from Genomic Sequences," identified by Ser. No. 11/351,951, filed on Feb. 10, 2006, which claims the benefit of U.S. Provisional Application No. 60/652,499, filed Feb. 11, 2005, the disclosures of which are incorporated by reference herein in their entirety.

The present application is related to U.S. patent application entitled "Ribonucleic Acid Interference Molecules," identified by Ser. No. 11/352,152, and filed on Feb. 10, 2006, the disclosure of which is incorporated by reference herein in its entirety. Also, the present application is related to U.S. patent application entitled "System and Method for Identification of MicroRNA Target Sites and Corresponding Targeting MicroRNA Sequences," identified by Ser. No. 11/351,821, and filed on Feb. 10, 2006, the disclosure of which is incorporated by reference herein in its entirety.

Additionally, the present application is related to U.S. patent application entitled "Ribonucleic Acid Interference Molecules and Binding Sites Derived by Analyzing Intergenic and Intronic Regions of Genomes," identified by Ser. No. 11/408,557, and filed on Apr. 21, 2006, the disclosure of which is incorporated by reference herein in its entirety.

The present application is also related to U.S. patent application Ser. No. 12/183,166 entitled "Ribonucleic Acid Interference Molecules of *Arabidopsis Thaliana*," and filed concurrently herewith.

FIELD OF THE INVENTION

The present invention relates to genes and, more particularly, to ribonucleic acid interference molecules and their role in the regulation of gene expression.
Lengthy Table The present application includes a lengthy table section filed electronically via EFS-Web that includes the following tables: "1500-774_Oryza_Precursor_Table." created on Jul. 31, 2008 and having a size of 2.06 megabytes (MB), and "1500-774_Oryza_Mature_Table," created on Jul. 31, 2008 and having a size of 1.25 MB, the contents of which are incorporated by reference herein.

A copy of the table section is available in electronic form from the USPTO web site (http://seqdata.uspto.gov/). An electronic copy of the table will also be available from the USPTO upon request and payment of the fee set forth in 37 CFR 1.19(b)(3).

BACKGROUND OF THE INVENTION

The ability of an organism to regulate the expression of its genes is of central importance. A breakdown in this homeostasis leads to disease states such as, for example, cancer, where a cell multiplies uncontrollably to the detriment of the organism. The general mechanisms utilized by organisms to maintain this gene expression homeostasis are the focus of intense scientific study.

Some cells are able to down-regulate their gene expression through certain ribonucleic acid (RNA) molecules. Namely, RNA molecules can act as potent gene expression regulators either by inducing messenger RNA (mRNA) degradation or by inhibiting translation. This activity is summarily referred to as post-transcriptional gene silencing (PTGS). An alternative name by which it is also known is RNA interference (RNAi). PTGS/RNAi has been found to function as a mediator of resistance to endogenous and exogenous pathogenic nucleic acid sequences, as well as a regulator of the expression of genes inside cells.

Early studies suggested only a limited role for RNAi, that of a defense mechanism against pathogens. However, the subsequent discovery of many endogenously-encoded microRNAs pointed towards the possibility of this being a more general, in nature, control mechanism. Recent evidence has led to conjecture that a wider spectrum of biological processes is affected by RNAi, thus extending the range of this presumed control layer.

A better understanding of the mechanism of the RNA interference process would benefit drug design, the fight against disease and the understanding of host defense mechanisms, among other things.

SUMMARY OF THE INVENTION

Sequences of ribonucleic acid interference molecules are provided. For example, in one aspect of the invention, at least one nucleic acid molecule including at least one of one or more precursor sequences having SEQ_ID NO: 1 through SEQ_ID NO: 11,928 and one or more corresponding mature sequences having SEQ_ID NO: 11,929 through SEQ_ID NO: 24,555 is provided.

In another aspect of the invention, a method for regulating gene expression comprises the following step. At least one nucleic acid molecule including at least one of one or more precursor sequences having SEQ_ID NO: 1 through SEQ_ID NO: 11,928 and one or more corresponding mature sequences having SEQ_ID NO: 11,929 through SEQ_ID NO: 24,555 is used to regulate the expression of one or more genes.

Also, in another aspect of the invention, a vector incorporating one or more sequences, wherein the one or more sequences comprises at least one of one or more precursor sequences having SEQ_ID NO: 1 through SEQ_ID NO: 11,928 and one or more corresponding mature sequences having SEQ_ID NO: 11,929 through SEQ_ID NO: 24,555 is provided. Further, in yet another aspect of the invention, a biochemical construct comprising a nucleic acid molecule, wherein the nucleic acid molecule comprises at least one of one or more precursor sequences having SEQ_ID NO: 1 through SEQ_ID NO: 11,928 and one or more corresponding mature sequences having SEQ_D NO: 11,929 through SEQ_ID NO: 24,555 is provided.

A more complete understanding of the present invention, as well as further features and advantages of the present invention, will be obtained by reference to the following detailed description.

DETAILED DESCRIPTION OF PREFERRED EMBODIMENTS

Principles of the present invention include ribonucleic acid (RNA) molecules and their role in gene expression regulation. The term "gene expression," as used herein, refers generally to the transcription of messenger RNA (mRNA) from a gene and its subsequent translation into a functional protein. One class of RNA molecules involved in gene expression regulation includes microRNAs, which are endogenously encoded and regulate gene expression by either disrupting the translation process or by degrading an mRNA transcript (thus, inducing post-transcriptional silencing of one or more target sequences).

MicroRNAs are transcribed as parts of longer primary transcripts known as pri-microRNAs. Pri-microRNAs are subsequently cleaved by Drosha, a double-stranded-RNA-specific ribonuclease, to form microRNA precursors or pre-microRNAs, but exceptions have also been reported (for example, mirtrons). Pre-microRNAs are exported by Exportin-5 from the nucleus into the cytoplasm where they are processed by Dicer. Dicer is a member of the RNase III family of nucleases that cleaves the pre-microRNA and forms a double-stranded RNA with 3' end overhangs that are typically two nucleotides long.

The mature microRNA is derived from either the leading or the lagging arm of the microRNA precursor. The double-stranded RNA species gets separated into its component single strands and the one corresponding to the mature microRNA becomes associated with the effector complex known as RNA-induced silencing complex (RISC). The RISC and attached microRNA base pairs with its target(s) in a sequence-directed manner using Watson-Crick pairing (and the occasional formation of G:U pairs).

As described herein, the target sequence(s) may be naturally occurring. Alternatively, the target sequences may be synthetically constructed. A target sequence may be synthetically constructed so as to, for example, test prediction methods and/or to induce the RNAi/PTGS control of genes of interest. Additionally, a target sequence may be synthetically constructed so as to control multiple genes with a single RNA molecule, as well as to modify, in a combinatorial manner, the kinetics of the reaction by, for example, introducing multiple target sites.

Similarly, the precursor sequence(s) may be either naturally occurring or synthetically constructed. For example, a precursor sequence of interest may be purified and synthetically constructed and introduced into a cell that lacks that particular precursor. Further, when any of the above sequences are naturally occurring, they may be synthetically isolated and purified, for analysis purposes, from the genome that contains them (for example, using standard molecular techniques).

The related U.S. patent applications identified above (that is, Ser. Nos. 11/352,152, 11/351,821, 11/351,951 and 11/408,557, the disclosures of which are incorporated by reference herein in their entirety) addressed several important questions. For example, given a nucleotide sequence, is the sequence part of or does it contain a microRNA precursor? Also, given the sequence of a microRNA precursor, what is the location of the segment which will give rise to the mature microRNA? Further, is there more than one mature microRNA produced by a particular precursor? And if so, what are the locations of the segments which, after transcription and processing, will give rise to these additional mature microRNAs?

Another question of interest is the following. Given the 3' untranslated region (3'UTR) of a gene of interest, which region(s) of it will function as a target(s) for some mature microRNA? This last question can also be asked when presented with the 5' untranslated region (5'UTR) or the amino acid coding region of a gene of interest, or any other transcribed sequence for that matter. Also, for a given putative target site, which among a set of candidate microRNAs, if any, will bind to the putative target site?

As described herein, U.S. patent application entitled "System and Method for Identification of MicroRNA Precursor Sequences and Corresponding Mature MicroRNA Sequences from Genomic Sequences," identified by Ser. No. 11/351,951 (the disclosure of which is incorporated by reference herein in its entirety) focuses on the problem of whether a specific nucleotide sequence corresponds to a microRNA precursor or to a mature microRNA.

The above-noted techniques include a first phase during which patterns are generated by processing an appropriate training set using a pattern discovery algorithm. If the training set includes sequences of microRNA precursors, then the generated patterns, after appropriate attribute-based filtering, will be microRNA-precursor-specific. If the training set includes sequences of mature microRNAs, then the generated patterns, after appropriate attribute-based filtering, will be mature-microRNA-specific. Alternatively, the training set can include putative mature microRNAs or putative microRNA precursors. In a preferred embodiment, two training sets are used, one including sequences of known microRNA precursors and one including sequences of known mature microRNAs.

The basic idea of this pattern-based technique is to replace the training set of sequences with an "equivalent" representation that includes patterns. The patterns can be derived using, for example, a pattern discovery algorithm, such as the Teiresias algorithm. See, for example, U.S. Pat. No. 6,108,666 issued to A. Floratos and I. Rigoutsos, entitled "Method and Apparatus for Pattern Discovery in 1-Dimensional Event Streams," the disclosure of which is incorporated by reference herein. The patterns are, preferably, maximal in composition and length (properties which are, by default, guaranteed by the Teiresias algorithm).

The generated microRNA-precursor-specific or mature-microRNA-specific patterns can be used as predicates to identify, in a de novo manner, microRNA precursors from a genomic sequence, or mature microRNAs in the sequence of a putative microRNA precursor. This is exploited in the technique's second phase, during which the patterns at hand are sought in the sequence under consideration. To determine whether a given nucleotide sequence S is part of, or encodes, a microRNA precursor, the microRNA-precursor-specific patterns are used. Also, to determine whether a given nucleotide sequence S corresponds to, or contains a mature microRNA, mature-microRNA-specific patterns are used.

In general, one anticipates numerous instances of microRNA-precursor-specific patterns in sequences that correspond to microRNA precursors whereas background and unrelated sequences should receive few or no such hits. If the number of pattern instances exceeds a predetermined threshold, then the corresponding segment of the sequence that receives the pattern support (and possibly an appropriately sized flanking region) is reported as a putative microRNA precursor. Analogous comments can be made about mature-microRNA-specific patterns and sequences containing mature microRNAs.

In one or more embodiments of the present invention, pattern-discovery techniques, such as those described above, are used in conjunction with publicly available genomic sequences to predict microRNA precursor and mature microRNA sequences related to the organism *Oryza sativa* (*O. sativa*) (the sequences were downloaded from the TAIR repository). Namely, predicted precursor sequences having SEQ_ID NO: 1 through SEQ_ID NO: 11,928 derived from the genome of *O. sativa* are presented. Also, predicted mature sequences having SEQ_ID NO: 11,929 through SEQ_ID NO: 24,555 derived from the corresponding predicted precursors of *O. sativa* are presented.

The aforementioned predicted precursor and mature sequences are submitted herewith in electronic text format via EFS-Web as the file "1500-774_SequenceProject_ST25_7.28.08," created on Jul. 28, 2008, having a size of 4.87 MB, the contents of which are incorporated by reference herein.

The sequences presented herein, whether precursors or matures, are DNA sequences. It should be appreciated, however, that one of ordinary skill in the art would easily be able to derive the RNA transcripts corresponding to these DNA sequences. As such, the RNA forms of these DNA sequences are considered to be within the scope of the present teachings. The global coordinates of the sequences described herein may change from one release of the genomic assembly to the next. Nonetheless, even though its location may change, the actual sequence that corresponds to a micro NA precursor and the corresponding mature microRNA are expected to remain unique and thus the corresponding sequence's new location will still be identifiable (except, of course, for the case where the sequence at hand corresponds to a segment that has been removed from the genomic assembly that is being examined).

One of ordinary skill in the art would also recognize that sequences that are either homologous or orthologous to the sequences presented herein, (for example, sequences that are related by vertical descent from a common ancestor or through other techniques (for example, through horizontal gene transfer)), will likely be present in genomes other than the ones mentioned herein. Such homologous and/or orthologous sequences are expected to generally differ from the sequences listed herein by only a small number of locations. Thus, the techniques described herein should be construed as being broadly applicable to such homologous and/or orthologous sequences from species other from those listed above.

According to an exemplary embodiment of the present invention, nucleic acid molecules may be generated based on the predicted precursor and mature sequences. The nucleic acid molecules generated may be used to regulate gene expression. As described generally above, mechanisms exist by which RNA molecules effect the expression of genes. By way of example only, the generated nucleic acid molecules may regulate the expression of a gene, or genes, by inducing post-transcriptional silencing of the gene (for example, as described above). Using the predicted precursor and mature sequences, study of gene expression may be conducted using techniques and procedures commonly known to those skilled in the art.

Assume, for example, that one is interested in modulating the expression of a given gene G. One can use a methodology such as the one described in U.S. patent application Ser. No. 11/351,821, filed on Feb. 10, 2006 and entitled "System and Method for Identification of MicroRNA Target Sites and Corresponding MicroRNA Sequences" to analyze the transcript of gene G and identify those of the mature sequences listed in the description herein that are predicted to target gene G as well as the locations along the transcript where such targeting occurs. This will provide a list L of microRNAs that are predicted to target gene G in a natural setting. One can also separately examine each microRNA, m, from the list, L, in turn, and determine the impact that expression of m can have on gene G. Additionally, one can also use information from microRNA profiling studies (for example, over time and/or across tissues) that show the level of expression of each of the microRNAs in L to determine the level of expression of G at a given time and/or in a given tissue. By employing a properly chosen subset from among the microRNAs in L, one can achieve a desired level of modulation of gene G at a given time point or given tissue.

As described herein, one or more embodiments of the present invention include the sequence of one or more nucleic acid molecules (for example, one or more isolated and purified nucleic acid molecules) of interest, wherein the sequence of the nucleic acid molecule of interest is at least one of one or more precursor sequences having SEQ_ID NO: 1 through SEQ_ID NO: 11,928 and its corresponding one or more mature sequences from among those having SEQ_ID NO: 11,929 through SEQ_ID NO: 24,555. One or more of the at least one of one or more precursor sequences and one or more mature sequences may be computationally predicted. The precursor sequences and mature sequences can be, for example, computationally predicted (for example, from publicly available genomes) using a pattern discovery method. Also, the at least one nucleic acid molecule can regulate the expression of a gene by inducing post-transcriptional silencing of that gene. The nucleic acid molecule can also, for example, encode ribonucleic acid sequences as well as encode interfering ribonucleic acid sequences.

The precursor sequences having SEQ_ID NO: 1 through SEQ_ID NO: 11,928 can be derived from a genomic sequence corresponding to O. saliva, and the mature sequences having SEQ_ID NO: 11,929 through SEQ_ID NO: 24,555 can be derived from a genomic sequence corresponding to O. sativa.

One or more embodiments of the present invention also include techniques for regulating gene expression by using at least one nucleic acid molecule (for example, an isolated and purified nucleic acid molecule) including at least one of one or more precursor sequences having SEQ_ID NO: 1 through SEQ_ID NO: 11,928 and their corresponding one or more mature sequences having SEQ_ID NO: 11,929 through SEQ_ID NO: 24,555 to regulate the expression of one or more genes.

One or more of the precursor or mature microRNA sequences can be, for example, synthetically removed from a genome that contains the one or more of the sequences naturally and/or the sequences can be synthetically constructed. Also, the sequences can be, for example, synthetically introduced in a genome that does not contain them naturally. In one or more embodiments of the invention, the sequences can also be transcribed at will, giving rise to one or more interfering ribonucleic acid molecules that induce post-transcriptional repression of one or more target sequences.

The above-noted techniques for regulating gene expression may also include, for example, introducing instances of the precursor microRNA of interest into an environment (for example, a cellular environment) where the nucleic acid molecule can be produced biochemically, giving rise to one or more interfering ribonucleic acid molecules that correspond to the mature microRNAs embedded in this precursor and affect one or more target sequences.

One or more embodiments of the present invention can also include a vector incorporating one or more sequences, wherein the one or more sequences comprises at least one of one or more precursor sequences having SEQ_ID NO: 1 through SEQ_ID NO: 11,928 and one or more corresponding mature sequences having SEQ_ID NO: 11,929 through SEQ_ID NO: 24,555.

Additionally, one or more embodiments of the present invention can also include a biochemical construct comprising a nucleic acid molecule (for example, an isolated and purified nucleic acid molecule), wherein the nucleic acid molecule includes at least one of one or more precursor sequences having SEQ_D NO: 1 through SEQ_ID NO: 11,928 and one or more corresponding mature sequences having SEQ_ID NO: 11,929 through SEQ_ID NO: 24,555.

Although illustrative embodiments of the present invention have been described herein, it is to be understood that the invention is not limited to those precise embodiments, and that various other changes and modifications may be made by one skilled in the art without departing from the scope or spirit of the invention. For example, one may modify one or more of the described precursor sequences by adding or removing a number of nucleotides that is small enough to not radically alter the original sequence's behavior. Also, one may insert one or more of the described mature microRNA sequences in an appropriately constructed "container sequence" (for example, a precursor-like construct that is different than the precursor where this mature sequence naturally occurs) that still permits the excision of effectively the same mature microRNA sequence, thus generating an active molecule whose action is essentially unchanged with respect to that of the molecule corresponding to the starting mature microRNA sequence.

SEQUENCE LISTING

The patent contains a lengthy "Sequence Listing" section. A copy of the "Sequence Listing" is available in electronic form from the USPTO web site (http://seqdata.uspto.gov/?pageRequest=docDetail&DocID=US08795987B2). An electronic copy of the "Sequence Listing" will also be available from the USPTO upon request and payment of the fee set forth in 37 CFR 1.19(b)(3).

What is claimed is:

1. A method for synthetically constructing a nucleic acid molecule from sequences related to *Oryza sativa*, the method comprising:
   predicting a microRNA precursor sequence related to *Oryza sativa*, wherein predicting a precursor sequence comprises:
      generating one or more patterns of conserved sequences by processing a collection of known microRNA precursor sequences related to *Oryza sativa* and applying a pattern discovery method to the collection of known microRNA precursor sequences to generate the one or more patterns;
      assigning one or more attributes to the one or more generated patterns;
      subselecting one or more candidate regions of a sample nucleotide sequence from at least one of an intergenic region and an intronic region in connection with using the one or more patterns whose one or more attributes satisfy at least one criterion; and
      using the one or more subselected candidate regions to predict one or more microRNA precursors in a nucleotide sequence related to *Oryza sativa* via filtering the one or more subselected candidate regions based on, for each pattern of sequences, structure energy and number of bulges;
   predicting a mature microRNA sequence related to *Oryza sativa*, wherein predicting a precursor sequence comprises:
      generating one or more patterns of conserved sequences by processing a collection of known mature microRNA sequences related to *Oryza sativa* and applying a pattern discovery method to the collection of known mature microRNA sequences to generate the one or more patterns;
      assigning one or more attributes to the one or more generated patterns;
      subselecting one or more candidate regions of a sample nucleotide sequence from at least one of an intergenic region and an intronic region in connection using the one or more patterns whose one or more attributes satisfy at least one criterion;
      using the one or more subselected candidate regions to predict one or more mature microRNA in a nucleotide sequence related to *Oryza sativa* via filtering the one or more subselected candidate regions based on, for each pattern of sequences, structure energy and number of bulges; and
   synthetically constructing a nucleic acid molecule based on a predicted microRNA precursor sequence and a predicted mature microRNA sequence.

2. The method of claim 1, further comprising introducing the nucleic acid molecule into an environment where the nucleic acid molecule can be produced biochemically.

3. The method of claim 1, wherein one or more of the sequences are synthetically removed from a genome that contains the one or more of the sequences naturally.

4. The method of claim 1, wherein one or more of the sequences are synthetically introduced in a genome that does not contain the one or more sequences naturally.

5. The method of claim 1, further comprising transcribing the one or more sequences, giving rise to one or more interfering ribonucleic acid molecules.

6. The method of claim 1, wherein one or more of the sequences are synthetically constructed.

7. The method of claim 1, wherein the predicted precursor sequence consists of SEQ_ID NO: 1, and the predicted corresponding mature sequence consist of SEQ_ID NO: 11,929.

* * * * *